(12) United States Patent
Bridle et al.

(10) Patent No.: US 7,341,572 B2
(45) Date of Patent: *Mar. 11, 2008

(54) INFUSOR WITH FLEXIBLE SHEATH

(75) Inventors: Mark Bridle, Newport Beach, CA (US); Larry Black, Costa Mesa, CA (US)

(73) Assignee: Baxter International Inc., Deerfield, IL (US)

( * ) Notice: Subject to any disclaimer, the term of this patent is extended or adjusted under 35 U.S.C. 154(b) by 175 days.

This patent is subject to a terminal disclaimer.

(21) Appl. No.: 10/376,363

(22) Filed: Feb. 28, 2003

(65) Prior Publication Data

US 2004/0171987 A1 Sep. 2, 2004

(51) Int. Cl.
*A61M 1/00* (2006.01)
*A61M 5/00* (2006.01)

(52) U.S. Cl. ..................... 604/153; 604/262

(58) Field of Classification Search ............. 604/93.01, 604/131, 132, 140, 146, 150, 151, 153, 246, 604/257, 262; 128/DIG. 12, DIG. 13; 222/92, 222/95, 96, 105, 106
See application file for complete search history.

(56) References Cited

U.S. PATENT DOCUMENTS

| | | | |
|---|---|---|---|
| 3,319,684 A * | 5/1967 | Calhoun ..................... 604/326 |
| 4,419,096 A | 12/1983 | Leeper et al. |
| 4,621,658 A | 11/1986 | Buezis et al. |
| 4,744,387 A | 5/1988 | Otteman |
| 4,904,239 A | 2/1990 | Winchell et al. |
| 5,141,022 A | 8/1992 | Black |
| 5,167,631 A * | 12/1992 | Thompson et al. .......... 604/132 |
| 5,284,481 A | 2/1994 | Soika et al. |
| 5,334,197 A * | 8/1994 | Kriesel et al. .............. 604/132 |
| 5,616,127 A * | 4/1997 | Smith .......................... 604/118 |
| 5,732,736 A | 3/1998 | Ollivier |
| 5,897,530 A | 4/1999 | Jackson |
| 6,273,117 B1 | 8/2001 | McPhee |
| 6,413,239 B1 * | 7/2002 | Burns et al. ................. 604/132 |
| 6,569,128 B1 * | 5/2003 | Christensen et al. ......... 604/246 |
| 6,892,755 B2 * | 5/2005 | Black ..................... 137/505.41 |

* cited by examiner

*Primary Examiner*—Kevin C. Sirmons
*Assistant Examiner*—Elizabeth MacNeill
(74) *Attorney, Agent, or Firm*—Jeffrey C. Nichols; Austin J. Foley; Bradford R. L. Price (57) ABSTRACT

An improved ambulatory infusion device for dispensing a fluid into a patient includes a flexible bladder enclosure including a sheath of flexible material having a first open end a closed second end. The first open end of the sheath is affixed to a rigid closure, and a bladder support is secured in fixed position relative to the closure. An elastic bladder is mounted on the bladder support and positioned inside the sheath for holding fluid to be dispensed. The closed second end of the sheath is free to conform to the body of the patient so that the device is comfortable when worn. In other aspects, a flow restrictor and a pressure regulator are provided.

25 Claims, 12 Drawing Sheets

INFUSOR WITH FLEXIBLE SHEATH

BACKGROUND OF THE INVENTION

The present invention relates generally to infusion devices for delivering fluids, and more particularly to ambulatory infusion devices and to flow regulators mounted therein.

Ambulatory pumps or infusors are used for delivering a predetermined quantity of a drug or other medication to a patient in a preselected time period (e.g., several hours or days) at a slow fluid flow rate. Such infusors are typically worn on the body of the patient. A conventional infusor, such as that shown in U.S. Pat. No. 5,897,530 (the '530 patent), includes an elastomeric bladder filled with fluid to be infused and a rigid, fluid-tight housing around the bladder. The rigid housing does not conform to the patient's body and thus is uncomfortable. An infusor shown in U.S. Pat. No. 5,284,481 includes a collapsible shell surrounding an elastic reservoir. The ends of the shell and reservoir are attached to rigid end caps which do not conform to the patient's body and are therefore uncomfortable.

The bladder does not provide for constant fluid pressure as the fluid is infused. Indeed, fluid pressure at the outlet of the bladder will tend to be relatively high at the beginning of infusion and again at the end of infusion. This variability of fluid pressure will cause higher flow rates at the beginning and at the end of infusion, which is undesirable.

Conventional infusors such as that shown in the '530 patent include a valve and a glass capillary flow restrictor downstream from the bladder for regulating fluid flow rate. The flow restrictor is relatively expensive due to its glass construction, and can break during shipping and use. The glass capillary is rigid and does not conform to the patient's body, making it uncomfortable.

SUMMARY OF THE INVENTION

Briefly, one aspect of this invention is directed to an improved ambulatory infusion device for dispensing a fluid into a patient. The device comprises a bladder enclosure including a sheath of flexible material having a first open end defining a mouth and a second closed end. The first open end of the sheath is affixed to a rigid closure, and a bladder support is secured in fixed position relative to the closure. An elastic bladder is mounted on the bladder support and positioned inside the sheath for holding fluid to be dispensed. The sheath extends from the closure toward the closed second end of the sheath spaced beyond the bladder. The closed second end of the sheath is free to conform to the body of the patient so that the device is comfortable when worn.

In another aspect of the invention, the closed second end of the sheath is free of attachment to the bladder support, e.g., to allow for folding of the sheath.

In yet another aspect, the ambulatory infusion device comprises a bladder having an interior volume for storing the fluid under pressure. A pressure regulator is in fluid communication with the bladder and a flow restrictor is in fluid communication with the pressure regulator and is positioned downstream therefrom. The flow restrictor has an inlet for receiving the fluid at an inlet pressure and an outlet for discharging the fluid at an outlet pressure. The flow restrictor is formed of flexible tubing having an inside diameter less than about 0.003 inches.

In another aspect of the invention, the ambulatory infusion device comprises a bladder enclosure comprising a sheath of flexible material having a first open end defining a mouth and a second closed end, the first open end being affixed to a rigid closure. A bladder support is secured in fixed position relative to the closure and an elastic bladder is mounted on the bladder support. The bladder is positioned inside the sheath and has an interior volume for storing the fluid under pressure. The sheath extends from the closure toward the closed second end of the sheath spaced beyond the bladder. The closed second end of the sheath is free to conform to the body of the patient so that the device is comfortable when worn. A pressure regulator is in fluid communication with the bladder. A flow restrictor is in fluid communication with the pressure regulator and is positioned downstream therefrom. The flow restrictor has an inlet for receiving the fluid at an inlet pressure and an outlet for discharging the fluid at an outlet pressure.

Other features of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF THE PREFERRED EMBODIMENT

Figure 1:
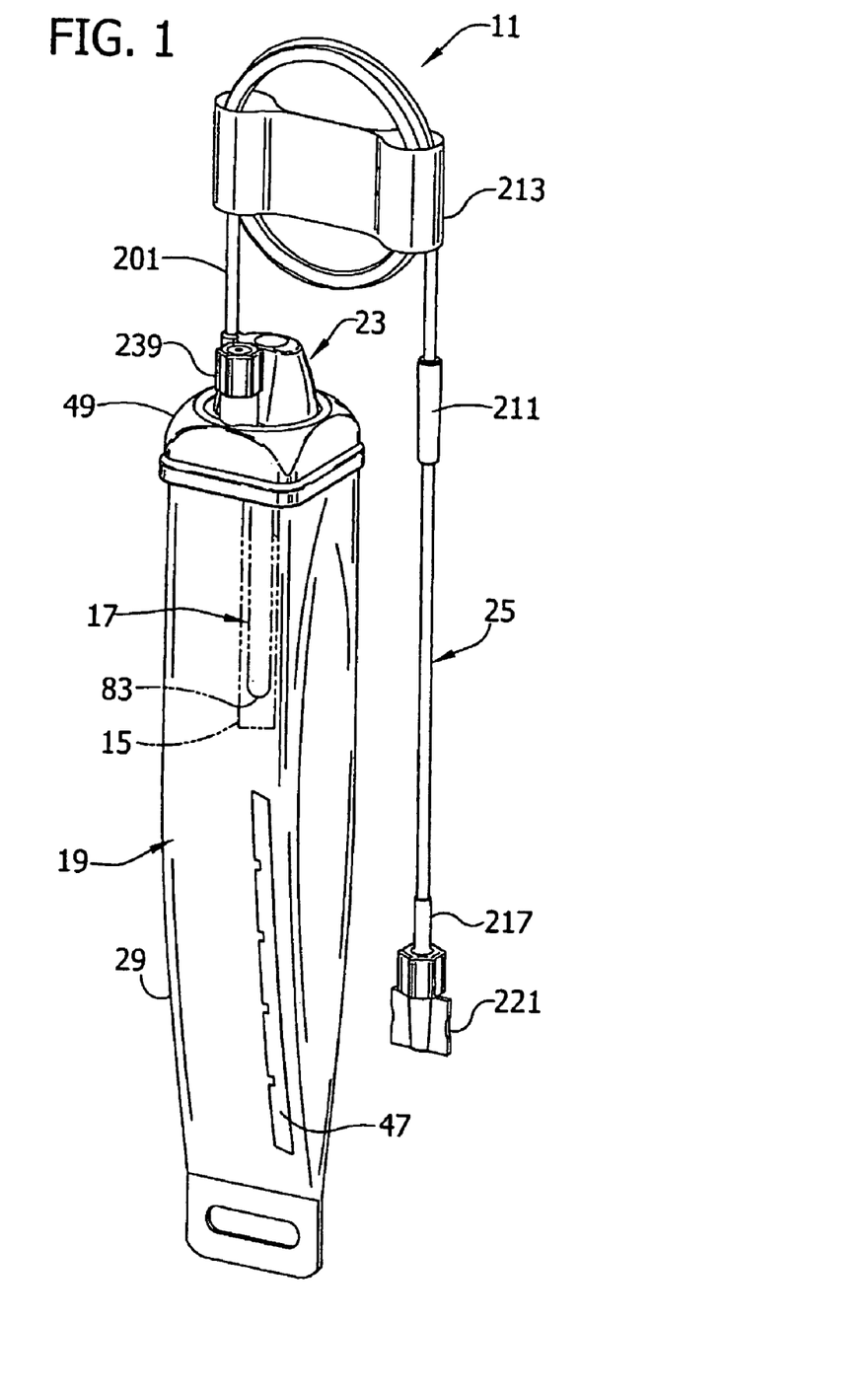
FIG. 1 is a perspective view of an infusion device of this invention.
Figure 2:
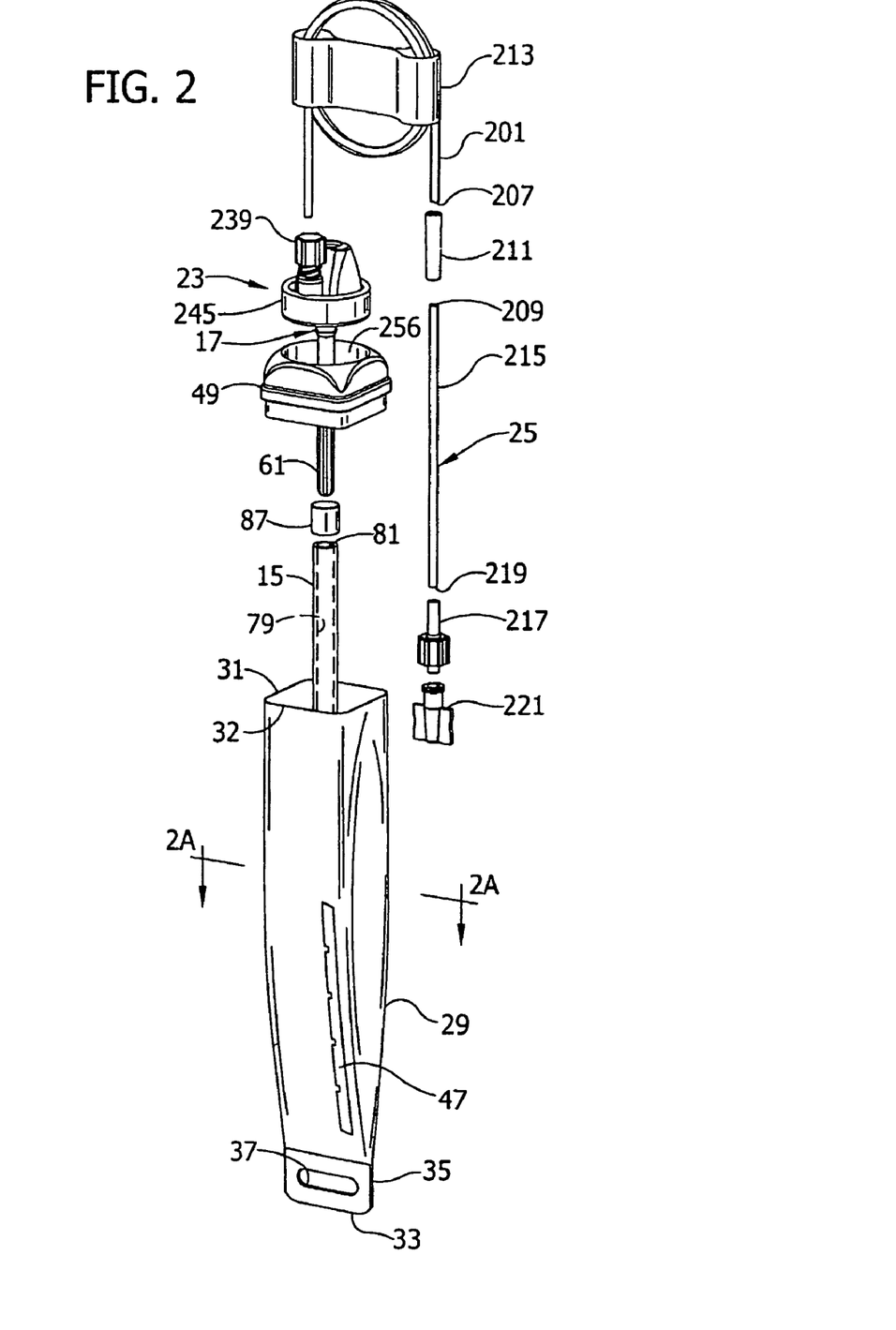
FIG. 2 is an exploded view of the infusion device of FIG. 1 including a pressure regulator and bladder support subassembly.

Referring now to the drawings and in particular to FIGS. 1 and 2, an ambulatory infusion device of the present invention is designated in its entirety by the reference numeral 11. The infusion device is adapted to dispense a therapeutic fluid, e.g., liquid medication, into a patient at a predetermined flow rate. The infusion device 11 generally comprises a bladder 15 for holding the fluid, a bladder support generally designated 17 for mounting the bladder, and a bladder enclosure generally designated 19 for enclosing the bladder. The device further includes a pressure regulator generally designated 23 (broadly, a closed-loop flow controlling system), and a flow restrictor generally designated 25, which, in a preferred embodiment, operate in conjunction with one another to maintain a substantially constant fluid flow to the patient until the fluid within the bladder 15 is exhausted.

The bladder enclosure 19 comprises a flexible sheath 29 having a first open end 31 defining a mouth 32 and a second end 33 closed by sealing, e.g., by thermal seal. The closed end of the sheath 29 includes a flat 35 having a slot 37 therein. Means for securing the closed end 33 to the patient, such as a strap (not shown) may be passed through the slot 37. Preferably, the closed end 33 is flexible so as to be comfortable against the body of the wearer. The sheath 29 is made of flexible, preferably resilient, material, e.g., polyethylene or vinyl, which is substantially transparent. The material preferably has "shape memory" properties, i.e., after it is initially formed, it regains its shape when it is not deformed by the bladder. The sheath 29 will not allow fluid to pass through it in case the bladder 15 ruptures. The bladder enclosure 19 may alternatively be a balloon or bag (not shown) having a closed end which is closed during manufacture, i.e., the closed end of the bladder enclosure need not be closed by an additional sealing step.

Figure 1A:
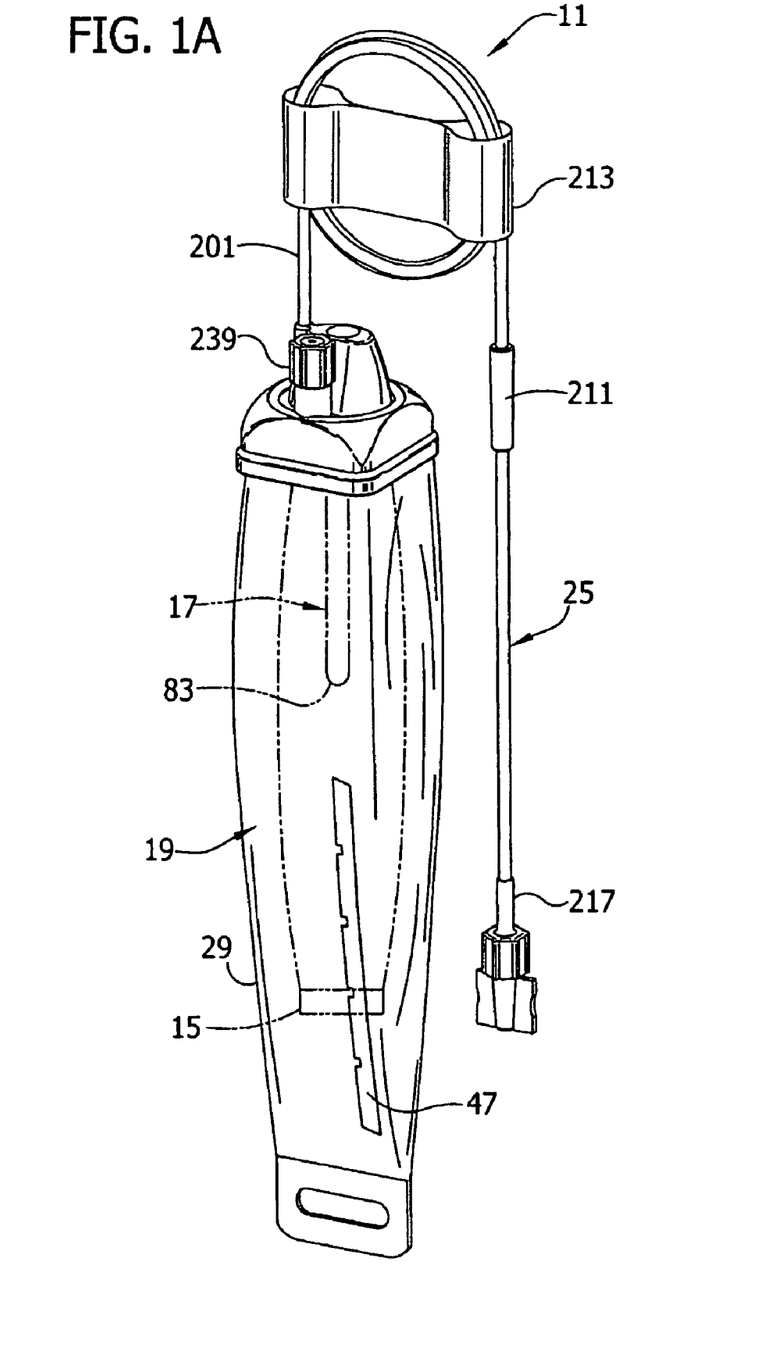
FIG. 1A is a perspective view of the infusion device showing a bladder (in phantom lines) filled with fluid within a bladder enclosure.
Figure 1B:
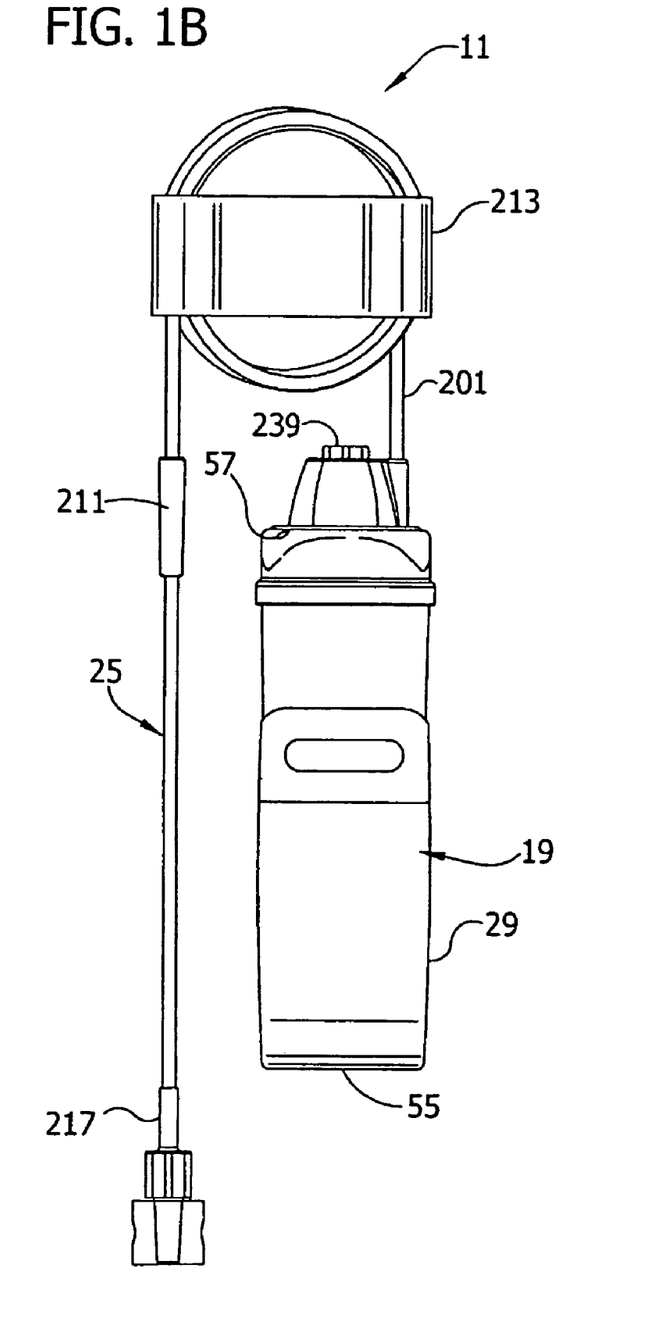
FIG. 1B is a perspective view of the infusion device showing the bladder enclosure folded over for compact storage of the device.
Figure 2A:
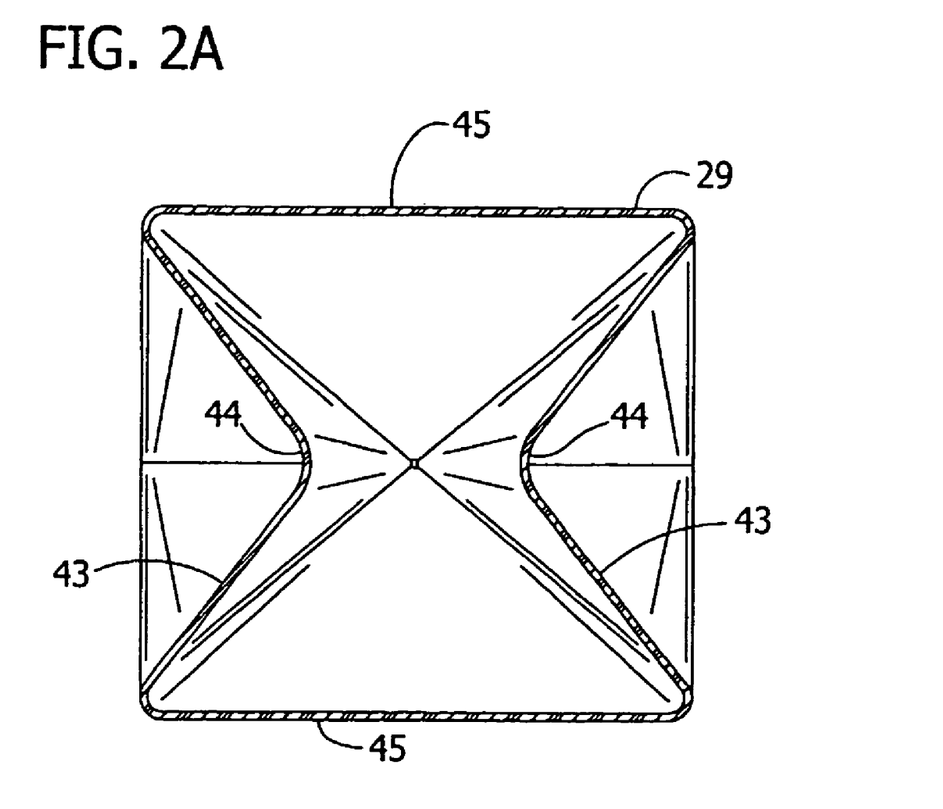
FIG. 2A is a section view taken along line 2A-2A of FIG. 2.

FIGS. 1, 1B and 2A illustrate the sheath 29 in a compact condition in which it has a folded shape. In the specific embodiment shown, the sheath has four sides, two opposing sides being designated 43 and the other two being designated 45. Sides 43 are folded along fold lines 44 extending lengthwise of the sheath 29 to form pleats which fold inward toward the bladder 15. One or both of the sides 45 of the sheath 29 include graduation marks 47 printed thereon to indicate the quantity of fluid in the bladder 15. As the bladder 15 is filled, it stretches and expands, causing the sheath 29 (the pleats) to unfold from, e.g., an unexpanded, folded condition, to an expanded condition (FIG. 1A) in which the material of the sheath may resiliently deform to accommodate the enlarged bladder. Thereafter, as fluid is dispensed from the bladder 15, the sheath 29 is adapted to collapse from its expanded condition toward its folded condition. Because the sheath 29 is made of resilient material, it tends to regain its folded (e.g., pleated) shape as it collapses.

A rigid closure 49 for closing the mouth 32 of the sheath 29 includes a lip 51 (FIG. 5) around its periphery which defines a groove 53 for receiving the first open end 31 of the sheath. The open end of the sheath 29 is affixed to the closure 49, as by heat sealing, preferably a conventional plastic welding process known as "through transmission infrared,"; and a fluid-tight seal is thus formed between the sheath and the closure. In this embodiment, the closure 49 is generally rectangular, but other shapes may be used within the scope of this invention. The sheath 29 extends from the closure 49 toward the closed end of the sheath. The length of the sheath 29 is such that the sheath extends beyond the bladder 15, and the closed end of the sheath is unattached to the bladder support 17. Preferably, the sheath 29 has a length which is greater than the length of the bladder 15 in its fully-filled condition. Also, the closed end of the sheath 29 is free to conform to the body of the patient so that the device is comfortable when worn. The closed second end 33 of the sheath 29 is also freely movable so that the sheath is foldable on one or more fold lines 55 (FIG. 1B) extending generally transverse to a longitudinal axis of the sheath for more compact storage of the infusion device 11. The closure 49 may include a hydrophobic vent 57 positioned adjacent one corner for venting air between the sheath 29 and bladder 15, while preventing the escape of liquid in the event of a bladder rupture.

Figure 3:
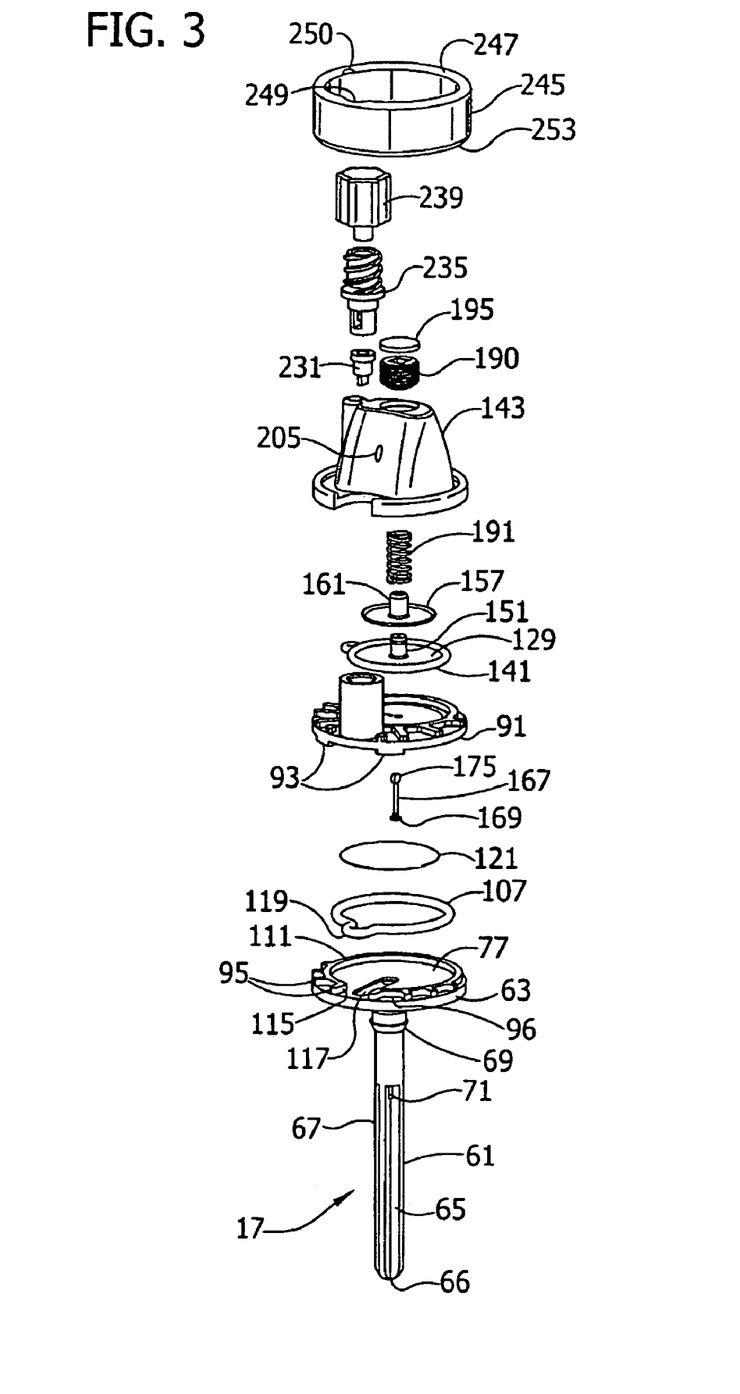
FIG. 3 is an exploded view of the regulator of the infusion device.
Figure 4:
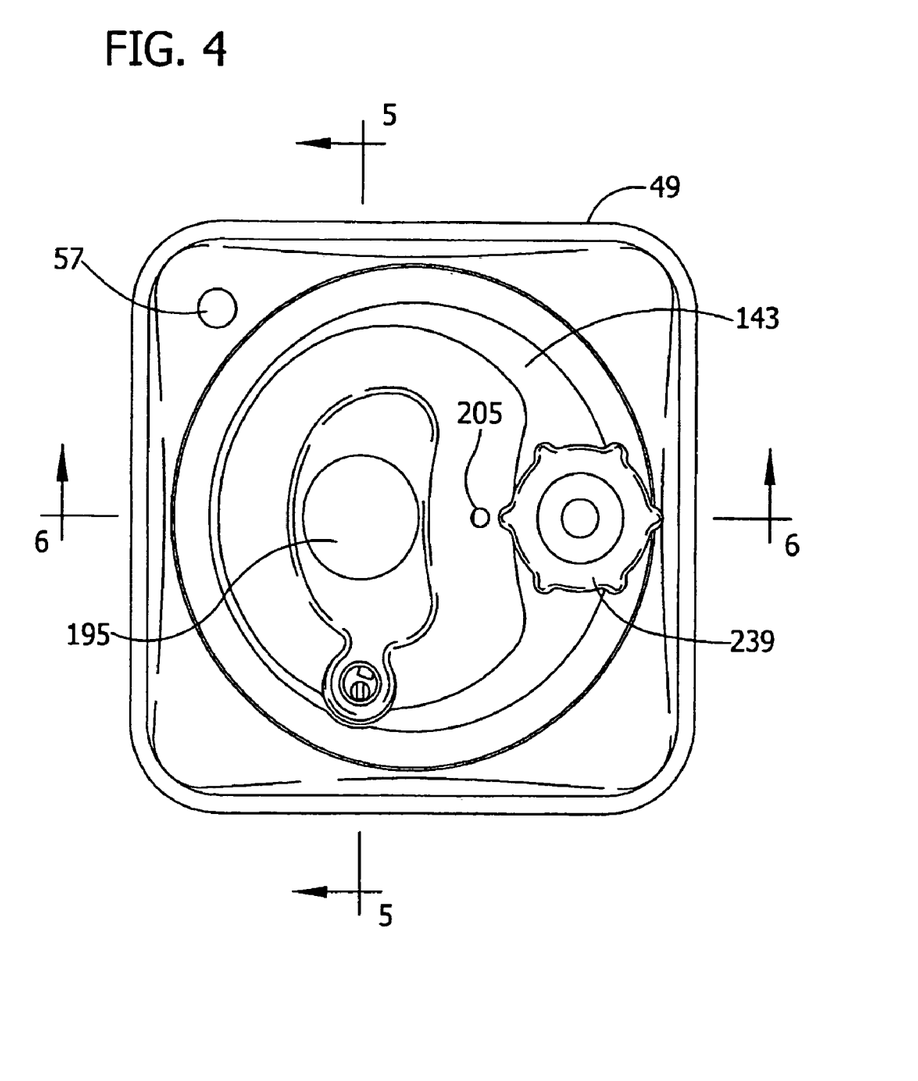
FIG. 4 is a top view of the infusion device with the fluid flow tubing omitted.

The bladder support 17 includes an elongate, generally cylindric stem 61 and a disk-shaped head 63 attached to a top end of the stem (as viewed in FIGS. 2-3). In this embodiment, the stem 61 and head 63 are formed of one piece of plastic, though other configurations and materials are contemplated within the scope of this invention. Longitudinally extending grooves 65 are formed in the stem 61, extending from a lower end 66 of the stem (as viewed in FIG. 3) to its central section 67. The grooves 65 aid in preventing the bladder 15 from adhering to the stem 61, allow for easier flow of the fluid, and to reduce the residual or remaining volume of medication at the end of the patient's infusion. The stem 61 includes two ring-shaped protrusions or barbs 69 adjacent the head 63 and engageable with the bladder 15 to help secure the bladder on the stem. A fluid inlet 71 formed in the central section 67 of the stem 61 (adjacent the ends of the grooves) is in fluid communication with a fluid passage 73 (FIGS. 5 and 6) extending longitudinally through the upper section of the stem and continuing through the head 63 to a head opening 75 in an upper surface 77 of the head opposite the stem. The central location of the inlet 71 substantially precludes any air trapped in the bladder during the filling process from reaching the inlet.

The bladder 15 (see FIGS. 1 and 2) is generally tubular, having an interior volume 79 for storing fluid under pressure, an open end 81 through which fluid may flow and a closed end 83. During assembly, the open end 81 of the bladder 15 is received over the stem 61 and is slid upward until the open end is adjacent a top end 85 (FIG. 6) of the stem and such that the bladder engages the two barbs 69. In this embodiment, the bladder 15 is secured to the stem 61 by wrapping the top of the bladder tightly with a heat-sealable, polyester-reinforced tape 87. The tape is wrapped under sufficient tension to ensure a liquid-tight seal between the bladder 15 and top end of the stem 85. The bladder 15 is suitably made of an elastic, resilient material, e.g., an elastomer such as rubber, though other materials may be used within the scope of this invention. However, the material should be compatible with the fluid that is to be contained within the bladder. Upon filling the bladder 15 with fluid, pressure is exerted on the fluid in the bladder due to the elasticity of the bladder.

Referring to FIGS. 3 and 6-8, the pressure regulator 23 includes a valve plate 91 seated on the head 63 of the bladder support 17. The valve plate is generally disk-shaped and includes two registration elements 93 on its lower side 94 facing the head 63 of the bladder support 17. The upper surface 77 of the head 63 includes ribs 95 which define recesses 96 for receiving the two registration elements 93 of the valve plate 91. The engagement of the registration elements and ribs 95 prevents relative rotational movement between the valve plate 91 and head 63.

Referring to FIGS. 3 and 5-8, the valve plate 91 further includes a circular boss 101 projecting downward from its lower side 94. A peripheral lip 105 extends down from the boss 101 and is surrounded by a resilient gasket 107 positioned between the head 63 and the valve plate 91. An annular rim 111 on the upper surface 77 of the head 63 defines a recess 113 for receiving the gasket. The rim 111 is centered slightly off the axis of the head opening 75 and has an opening 115 (see FIG. 3) which opens outwardly adjacent to a groove 117 in the upper side of the head 63. The groove extends radially from the head opening 75 to adjacent the edge of the upper surface 77 of the head 63. The gasket 107 is generally circular but includes an ear 119 extending outwardly into the opening 115 in the rim 111. A thin circular filter 121 is received within the lip 105 of the boss 101 and attached to the lip by heat sealing. The filter is Corporation of Bedford, Mass. A web of channels 102 or surface texture may be included on the boss 101 to provide a flow path for fluid between the filter 121 and surface of the boss 101.

Figure 8:
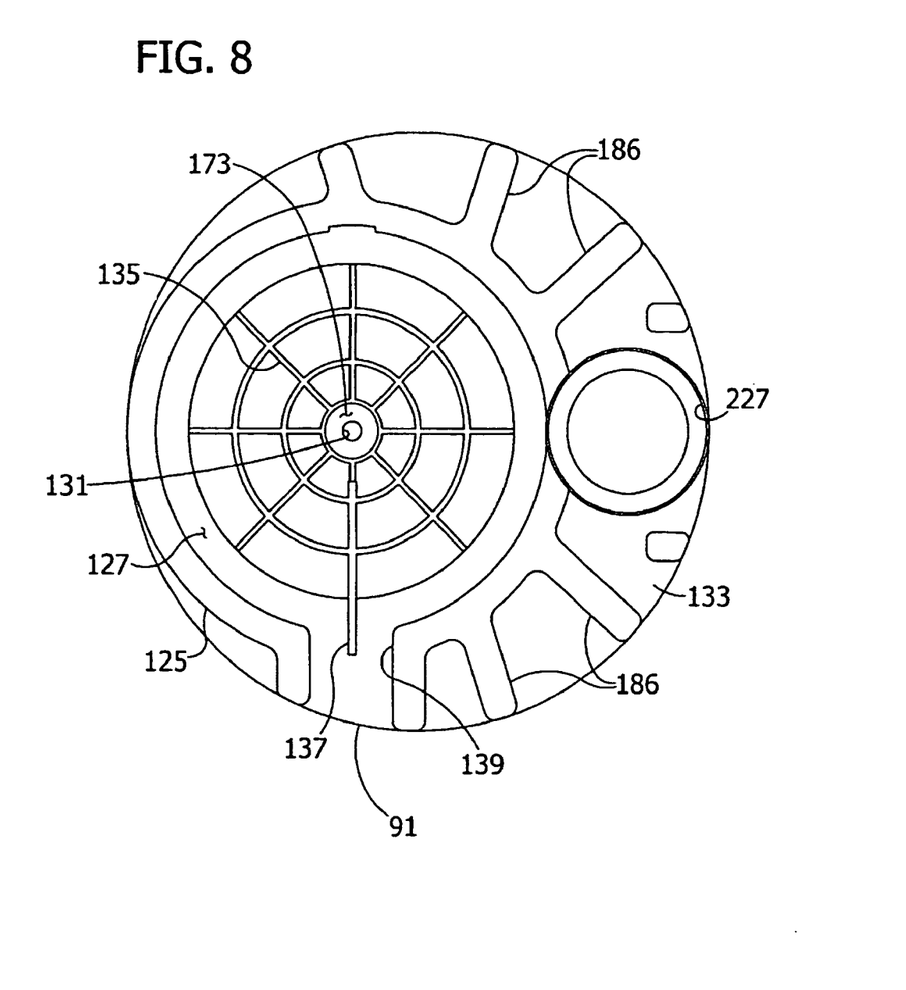
FIG. 8 is a top view of the valve plate.

Still referring to FIGS. 3 and 5-8, the upper side 133 of the valve plate 91 includes a generally circular wall 125 defining a cavity 127 for receiving a diaphragm 129. A hole 131 at the center of the cavity extends through the valve plate 91 from its upper side 133 to its lower side 94, a lower end of the hole defining an inlet 134 of the pressure regulator 23. The hole 131 is not coincident with the center of the boss 101 on the lower side 94 of the valve plate 91 or the center of the valve plate 91. The cavity 127 includes a plurality of channels 135 formed into the upper side 133 of the valve plate 91. In this embodiment, the channels 135 are formed in a circular web pattern. The channels cause substantially the entire lower surface of the diaphragm 129 to be exposed to the pressure of fluid flowing through the valve when the device is initially filled. In addition, the channels provide a fluid flow path to the main flow channel 137 which extends radially outward from adjacent the hole 131 in the valve plate 91 through a break 139 in the circular wall 125 (FIG. 8). Instead of channels, the valve plate 91 may have a textured surface to accomplish the same functions.

Figure 5:
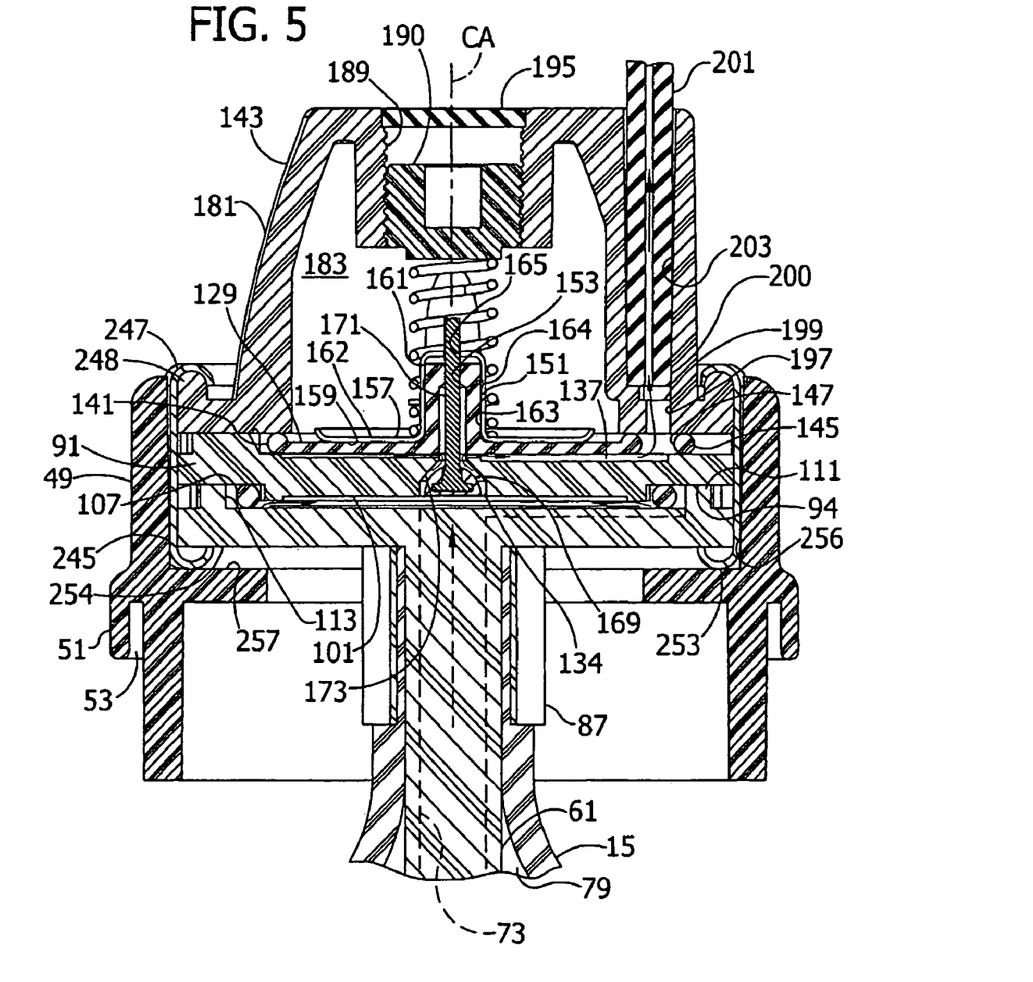
FIG. 5 is a section view taken along line 5-5 of FIG. 4 showing a portion of the filled bladder and a fluid flow path from the bladder.

The diaphragm 129 is disk-shaped and includes a brim 141 for engaging the circular wall 125 defining the cavity 127. The brim 141 of the diaphragm 129 is squeezed between the valve plate 91 and a cap 143 (described below) such that the only fluid path from beneath the diaphragm is through the main flow channel 137 (FIGS. 5 and 8). A fluid flow ring 145, which defines a hole 147 therein, projects from the periphery of the diaphragm 129 into the break 139 in the circular wall 125. The hole 147 in the ring 145 is aligned with an outlet of the main flow channel 137 for fluid communication therewith. The diaphragm is flexible, resilient and is preferably made of silicon rubber formed by injection or compression molding.

Figure 6:
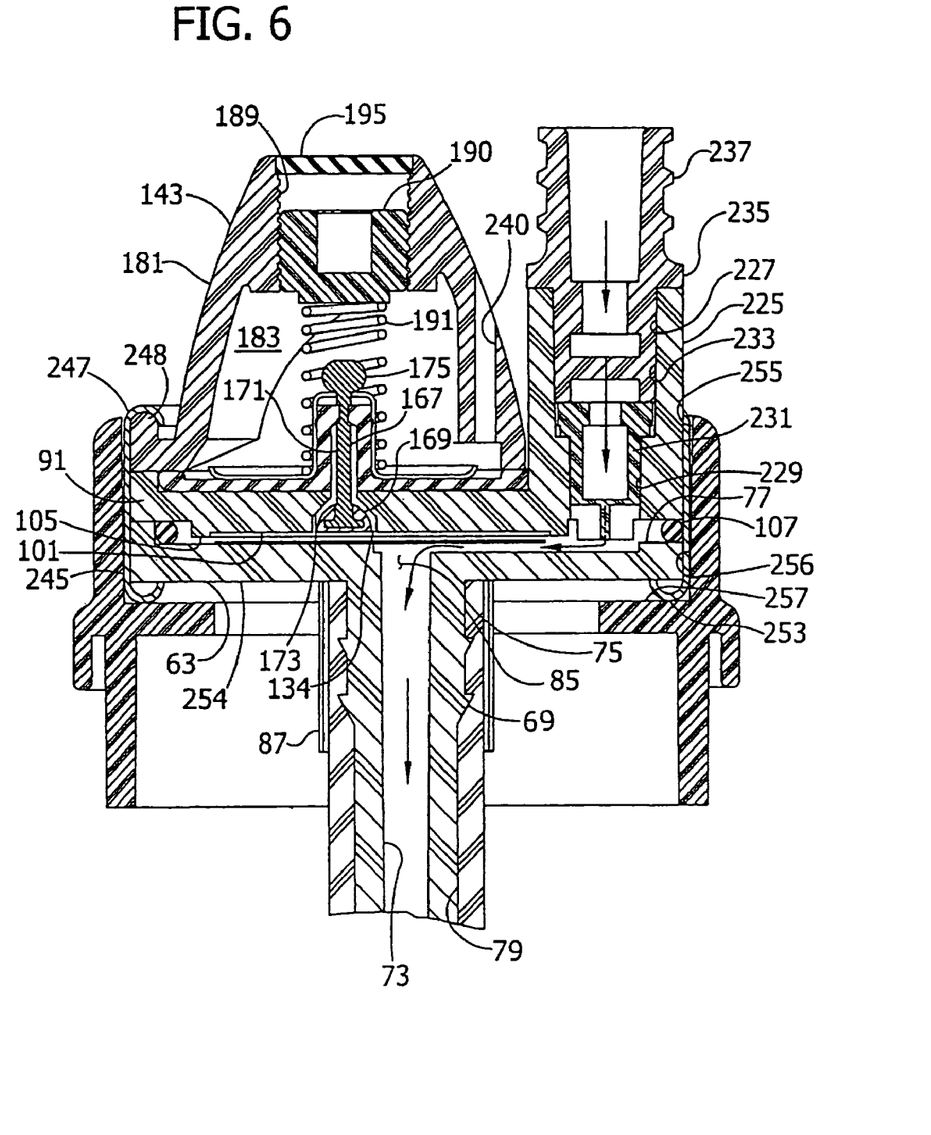
FIG. 6 is a section view taken along line 6-6 of FIG. 4.
Figure 7:
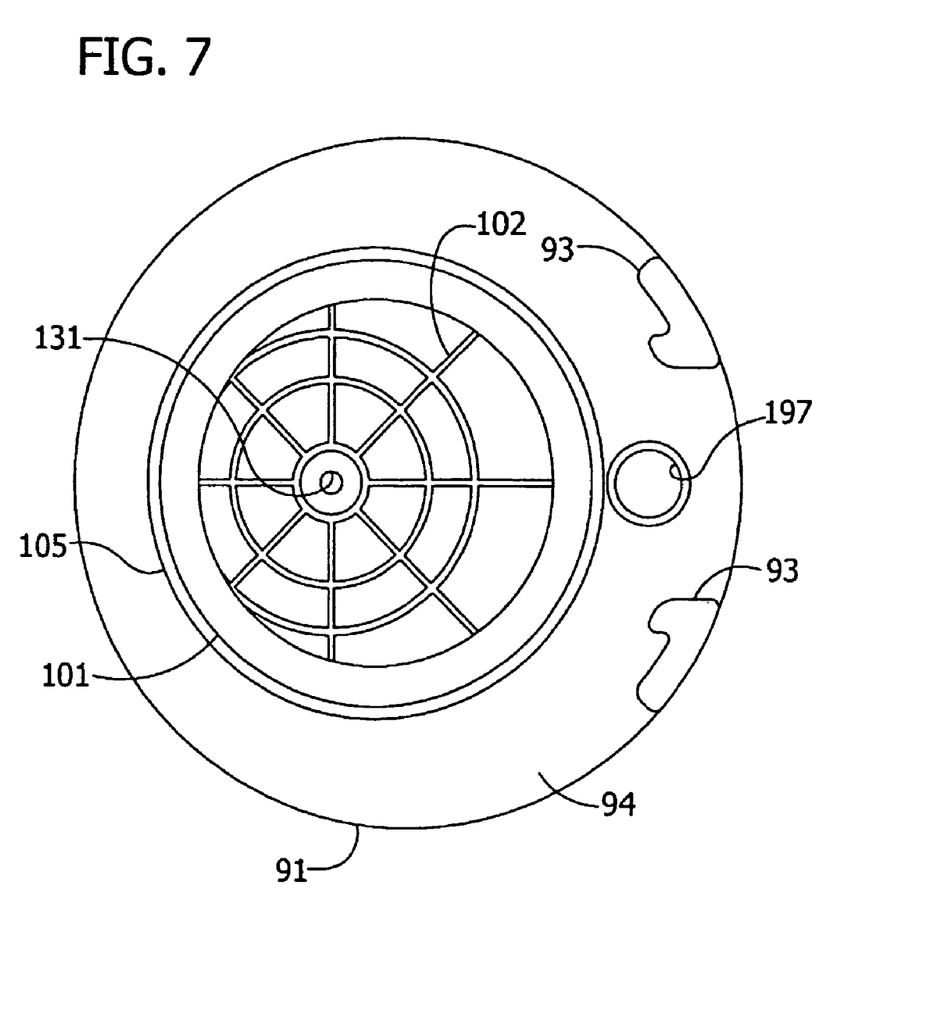
FIG. 7 is a bottom view of a valve plate.

Referring especially to FIGS. 5 and 6, the diaphragm 129 includes a stud 151 projecting from an upper side of the diaphragm and centered on a central axis CA of the diaphragm. A central passage 153 through the stud 151 is also centered on the central axis. The central passage 153 has a larger diameter at its lower portion than at its upper portion. A diaphragm backing or support plate 157 is also disk-shaped and includes a lower side 159 adapted for engaging the diaphragm. A central hollow hub 161 extends from an upper side 162 of the backing plate 157 and forms a socket 163 for receiving the stud 151 of the diaphragm 129.

The stud preferably includes an annular protrusion 164 to help in its molding process and increase the sealing force against the valve stem 171. The central hub 161 has a central aperture 165 therethrough. The backing plate 157 is made of a rigid material, e.g., aluminum.

The pressure regulator 23 comprises a valve 167 having a hemispheric head 169 and a stem 171 which extends through the hole 131 of the valve plate 91, the central passage 153 of the diaphragm 129 and the central aperture 165 of the backing plate 157. The hole 131 of the valve plate 91 is partially defined by a frustoconic seat 173 which opens downward toward the head 63 of the bladder support 17 and is adapted to receive the hemispheric head 169 of the valve 167 so that the head and seat cooperate to create a fluid flow path therebetween and to promote uniform fluid flow therebetween. The valve stem 171 is suitably made of a stiff material such as metal, and an elastomeric material covers the hemispheric head 169.

A tail end 175 (FIG. 6) of the valve stem 171 is deformed such as by crimping during assembly of the flow regulator so that the tail end engages the hub 161 of the backing plate 157 and preferably causes metal-to-metal contact. In response to fluid pressure and accompanying movement of the diaphragm 129 as described below, the valve 167 will move with the diaphragm and the backing plate 157.

In a preferred embodiment, the metal-to-metal contact between the deformed tail end of the valve stem 175 and the central aperature 165 of the backing plate 157 is such that movement of the backing plate away from the valve plate 91 (downward in FIG. 6) is fully transmitted directly to the valve 167, whereas movement of the backing plate in the other direction is not necessarily fully transmitted to the valve. In other words, movement of the backing plate along the axis of the valve stem 175, at least in one direction, is fully transmitted to the valve. The central aperature 165 in the backing plate 157 is sized to permit the valve stem 171 and attached hemispherical head 169 to "wiggle" or pivot in order to minimize radial forces between the frustoconic seat 173 and elastic hemispherical head 169 of the valve thus minimizing the head's distortion when in its flow-regulating position. The stem 171 also preferably engages the diaphragm 129 at its central passage 153 in a manner which provides a fluid tight seal, but due to the elastomeric material of the diaphragm the fit is such as to allow the stem and valve head 169 to "wiggle" or pivot.

As will be understood by those of skill in the art, the shape of the valve head 169 and the seat 173 also causes the valve head to substantially self-center within the seat so that a minimum of force is required to affect the gap between the head and seat surface. In this way, even if the valve plate 91, diaphragm 129 and backing plate 157 are not perfectly aligned, e.g., due to relatively loose dimensional tolerances or the device 11 being oriented at some angle to the position shown (sideways, etc.), the head 169 will still self center and the valve 167 is still effective. Accordingly, the valve 167, valve plate 91, diaphragm 129 and backing plate 157 are easier to manufacture because the dimensional tolerance for each of these elements may be relatively loose.

The cap 143 includes a housing 181 defining a cavity 183 therein for receiving the tail end 175 of the valve 167, the backing plate hub 161 and the diaphragm stud 151. A lower surface of the cap 143 is shaped to engage the brim 141 of the diaphragm 129 and the wall 125 and ribs 186 (FIG. 8) of the valve plate 91. A threaded opening 189 in an upper end of the housing 181 is threadably engaged by a set screw 190 which bears against a helical compression spring 191 (FIG. 6).

The spring 191 surrounds the backing plate hub 161 and is compressed between the backing plate 157 and the screw 190. Other biasing means could be used in place of or in addition to the spring 191. The spring 191 contacts the backing plate 157 to supply a biasing force to counteract the force exerted on the diaphragm 129 by the pressurized fluid. The backing plate 157 spreads the force supplied by the spring 191 around much of the surface area of the diaphragm 129 in a manner similar to the distribution of the force of the fluid on the opposing side of the diaphragm. The plate also serves to inhibit "creep" or stretching of the diaphragm 129 during the infusion period.

The spring 191 preferably has a relatively low spring constant, and more preferably has a spring constant of about 3.5 lbs/in. A seal 195, e.g., of epoxy or hot melt adhesive, may be placed over the screw 190 to prevent further adjustment of the screw after it is adjusted as described below.

As shown in FIG. 6, the cap 143 of the pressure regulator may include an air vent 240. The vent ensures that air pressure within the cavity 183 is the same as atmospheric pressure.

As shown in FIG. 5, the cap 143 includes a fluid passage 197 in fluid communication with the hole 147 in the fluid flow ring 145 of the diaphragm 129. An outlet 199 at the upper end of the passage 197 (as viewed in FIG. 5) constitutes the outlet of the pressure regulator 23. The outlet 199 is in fluid communication with an upstream end 200 of intermediate tubing 201 that is received in an elongate receiver 203 of the cap 143.

Referring to FIGS. 1 and 2, the pressure regulator 23 of this embodiment is connected to the flow restrictor 25 via the flexible intermediate tubing 201, though other means of connection are contemplated. The intermediate tubing has an inside diameter of about 0.025 inches. A downstream end 207 of the intermediate tubing 201 is connected to an inlet end 209 of the flow restrictor 25 by a first connector 211. The intermediate tubing 201 may be secured in a coiled position by suitable means such as adhesive tape 213, or by a conventional reel (not shown).

The flow restrictor 25 is formed of flexible tubing 215 having an inside diameter as required to achieve a desired flow rate when operated at a specific pressure within the adjustment range of the regulator. For example, a suitable inside diameter is less than 0.003 inches and more preferably in the range of about 0.010 to about 0.0022 inches. The flexible tubing 215 of the flow restrictor 25 is preferably made of polymeric material, such as polyolefin. The flow restrictor 25 causes a significant fluid pressure drop from its inlet end 209 to its outlet end 219.

Note that the pressure at the inlet end 209 of the flow restrictor 25 will be substantially the same as the pressure at the outlet end 199 of the pressure regulator 23. The pressure at the outlet end 219 of the flow restrictor 25 will be substantially the same as a vein pressure of the patient. The vein pressure is known and is substantially constant. The length of the tubing 215 of the fluid restrictor 25 is set such that, when the fluid is at a specific pressure within the pressure adjustment range of the regulator, the fluid will flow at a desired flow rate that is in accordance with the labeling of the infusion device such as 0.5 or 1.0 ml/hr. The tubing length for the restrictor 25 is typically around 4 inches. However, the inside diameter of the tubing 215 may vary during its manufacturing process, and such variance affects the flow rate through the tubing. The preferred pressure adjustment range for the regulator is about 7 to 9 pounds per square inch. Accordingly, the tubing length is cut such that, when the fluid is at a specific pressure within this adjustment range, the flow through the restrictor 25 will be at the desired flow rate. To set the restrictor's flow rate, an initial sample length of tubing 215 is cut and air of a known and desired pressure is forced through the tubing. The flow rate of the air is correlated to the desired flow rate of fluid and thus a measurement can be made of whether the tubing is at the appropriate length. If the flow rate of the air correlates to the desired fluid flow rate, the tubing 215 is used. If the air flow rate does not correlate to the desired fluid flow rate, the tubing is discarded, and the next length of tubing 215 is cut longer if the discarded length's flow rate was too high, and shorter if the discarded length's flow rate was too low. The air flow rate of each piece of tubing 215 may be used to adjust the cut length of the next piece to keep the flow rates relatively "centered" within an acceptable range of flow rates. Because the variability of the inside diameter is gradual over the length of a spool of tubing, one skilled in the art can determine whether to begin to increase the length of the tubing or shorten the length in a gradual manner so that the possibility of having discard (or rework) the tubing is remote.

A second connector 217 is attached to the outlet end 219 of the flow restrictor 25. The second connector 217 is suitably a male luer-type connector adapted to connect the infusion device 11 to a catheter of the patient. As shown, a cap 221 protects an outlet of the second connector.

Referring again to FIG. 6, a tubular projection 225 extending from an edge of the valve plate 91 defines a bore 227 having a lower section 229 for receiving a one-way valve 231, e.g., a duckbill valve, and an upper section 233 for receiving a conventional, luer-type fillport 235 that is secured by welding or bonding in the bore. The fillport includes external threads 237 for engaging internal threads of a syringe or like device for filling the bladder 15. The fillport may be provided with a cap 239 as shown in FIG. 1.

Referring to FIGS. 2-3 and 5-6, a rigid cylindric casing 245 is sized to receive the pressure regulator 23 and the head 63 of the bladder support 17 and is adapted to secure the cap 143 of the pressure regulator 23 to the head 63. The casing 245 has an in-turned upper edge 247 which engages a lip 248 on the cap 143 (see FIG. 6). Two small cut-outs 249, 250 (see FIG. 3) are formed in the upper edge 247 of the casing 245 to receive the projection 225 of the valve plate 91 and the receiver 203 of the cap 143, respectively. After the pressure regulator 23 and the head 63 are received in the casing 245, a lower edge 253 of the casing is in-turned or crimped to engage a lower surface 254 of the head while compressing the sealing brim 141 of the diaphragm 129 and the gasket 107. The casing 245, including the pressure regulator 23 and bladder support head 63 therein, is received in a cavity 255 defined by a side wall 256 of the rigid closure 49. The lower edge 253 of the casing 245 is located against an annular shelf 257 of the closure 49. The casing 245 is secured to the closure 49 by, for example, a press fit, or adhesive bond which forms a sufficient fluid-tight seal so that if the bladder 15 ruptures, the fluid released from the bladder will be substantially contained within the sheath 29. Note that the sheath is sealed at its open end 31 by the closure 49. The bladder support head 63 and the casing 245 serve to seal the closure 49. The casing 49 of this embodiment is made of metal, e.g., aluminum to facilitate the crimping.

Referring to FIGS. 1, 3 and 6, in use the bladder 15 is filled (typically by a pharmacist) by removing the fillport cap 239, attaching a syringe or other supply source, and injecting a fluid. The fluid passes through the one-way valve 231, into the groove 117 in the head 63, past the filter 121, into the fluid passage 73 of the bladder support 17 and into the bladder 15. The resilient, elastic bladder 15 stretches as it is filled so that the fluid is under pressure within the bladder. After the syringe is disconnected, the cap 239 is replaced on the fillport 235. The one-way valve 231 prevents the fluid inside the bladder 15 from escaping through the fillport. The patient may thereafter attach the second connector 217 to a catheter, the second end 33 of the sheath 29 to his or her clothing and secure, e.g., tape the flow restrictor to his or her skin as further described below. A priming operation may be required to exhaust air from the device 11.

Referring to FIGS. 1 and 5, once the second connector 217 is connected to the patient, the basic fluid path is from the bladder 15 through the passage 73 of the bladder support 17, through the filter 121, through the pressure regulator 23, the intermediate tubing 201, the flow restrictor 25 and then out of the device 11 through the second connector 217. In detail, the fluid will flow from the passage 73 of the bladder support 17 into the gap between the bladder support head 63 and the filter 121, through the filter 121 and into the inlet 134 of the pressure regulator 23. The fluid passes between the hemispherical valve head 169 and frustoconical seat 173, and through the hole 131 in the valve plate 91. The fluid then flows between the valve plate 91 and the underside of the diaphragm 129, e.g., in the channels (and/or texture) in the upper side 133 of the valve plate. The fluid then passes through the main flow channel 137, the hole 147 in the ring 145 of the diaphragm 129, and the fluid passage 197 of the cap. The fluid exits the pressure regulator 23 through the outlet 199 of the passage. Thereafter, the fluid is transferred from the pressure regulator 23 to the flow restrictor 25 through the intermediate tubing 201. Due to the narrow inside diameter of the flow restrictor 25, fluid slowly passes through the flow restrictor, the second connector 217 and into the catheter or other device attached to the patient. As noted above, the infusion device 11 is designed to deliver fluid at a substantially constant flow rate, such as 0.5 or 1.0 ml/hr.

Fluid pressure at the inlet 134 of the pressure regulator 23 should be higher than at the outlet 199. Moreover, the fluid pressure at the inlet 34 varies due to the bladder and the volume of fluid contained therein, as further described below. The pressure regulator 23 maintains the outlet pressure within a predetermined range of pressure so that the pressure of the fluid exiting the regulator is substantially constant.

Generally, the pressure drop across the restrictor 25 from its inlet 209 to its outlet 219 must remain within a specified tolerance in order to achieve the desired flow rate. Also, the flow rate through the regulator 23 must equal the flow rate through the restrictor 25 and the resulting flow rate into the patient. For the pressure at the restrictor inlet 209 to remain within its specified tolerance, the pressure drop between the regulator inlet 134 and outlet 199 must vary as the regulator inlet pressure changes, e.g., in relation to the volume of fluid remaining in the bladder. As the regulator inlet pressure changes, the flow rate through the regulator 23 changes. An increase in inlet pressure results in an increase in flow, and a decrease in inlet pressure causes a decrease in flow. A change in the flow rate between the valve head 169 and frustoconical seat 173 results in a change in the pressure at the outlet 199, such pressure acting on the movable diaphragm 129. An increase in flow results in an increase in pressure, and a decrease in flow results in a decrease in pressure. The resulting force exerted by the pressure of the fluid on the lower surface of the movable diaphragm 129 is preferably opposed by the forces resulting from the compression of the spring 191, deflection of the elastic diaphragm 129, and the distortion of the hemispheric head 169 against its frustoconic seat 173. A small change in the pressure acting on the diaphragm 129 (resulting from a change in the flow rate between the valve head 169 and seat 173) changes the force applied by the diaphragm on the valve, and consequently changes the force applied by the valve head to the seat. An increase in pressure on the diaphragm 129 results in an increased valve head-to-seat force, and a decrease in diaphragm pressure decreases the valve head-to-seat force. An increase in the valve head-to-seat force causes the valve head to move or deform so as to reduce the flow area between the valve and seat through which the fluid may flow. In contrast, a decrease in the valve head-to-seat force force results in an increase in the flow area. The changes in the flow area between the valve head 169 and seat 173 result in a change in the fluid flow rate therethrough. An increase in the flow area increases flow rate and the resulting force on the diaphragm 129, and a decrease in the flow area reduces flow rate and the resulting pressure on the diaphragm. As will be understood by those of skill in the art, the regulator 23 constitutes a closed-loop flow controlling system.

Preferably, the pressure regulator 23 is adapted to maintain the outlet pressure within the predetermined range even where the inlet pressure may be up to about 5 or more times greater than the desired outlet pressure. Other types of pressure regulators are contemplated within the scope of this invention.

The predetermined range of outlet pressure may be varied by the choice of the spring constant and the adjustment of the screw 190. Adjustment of the screw causes a change in the length of the spring 191 and thus causes a change in the biasing force against the diaphragm 129. Downward adjustment of the screw 190 (as viewed in FIG. 5) will increase the biasing force exerted by the spring 191 against the diaphragm 129 and attached valve 167 and will thereby cause an increase in the flow area between the valve head 169 and seat 173. This increase causes a decreased pressure drop across the valve head and seat and a resulting increase in the predetermined range of outlet pressure from the regulator. Similarly, upward adjustment of the screw 190 will decrease the biasing force exerted by the spring 191, resulting in a decrease in the flow area, an increase in the pressure drop, and a decrease in the predetermined range of outlet pressure of the regulator.

This ability to adjust the outlet pressure of the pressure regulator 23 is beneficial in "marrying" the flow restrictor 25 to the pressure regulator so that during use the desired flow rate is achieved. To marry the regulator 23 to the restrictor 25, the intermediate tubing 201 and flow restrictor 25 are attached to the assembled flow regulator 23 but before attachment of the bladder 15 to the stem 61, air of a pressure approximately the same as would be produced by the bladder is provided to the regulator via the fluid inlet 71. The set screw 190 is rotated until a desired flow rate of air is achieved. This desired flow rate is indicative of the fluid flow rate and thereby the regulator 23 can be set to produce the device's labeled flow rate.

Because the fluid flow resistance of the flow restrictor 25 may vary due to temperature changes and thus cause a change in the fluid flow rate through the device, it is preferred that the flow restrictor be maintained at a substantially constant temperature. Preferably, in accordance with a method of the present invention, the flow restrictor 25 is secured against the skin of the patient (e.g., by adhesive tape) so as to promote a relatively constant and predictable temperature of the flow restrictor. Securing the flow restrictor 25 against the skin ensures that the inside diameter and length of the flow restrictor, as well as the temperature and resulting viscosity of the fluid in the flow restrictor, remain substantially constant.

Figure 9:
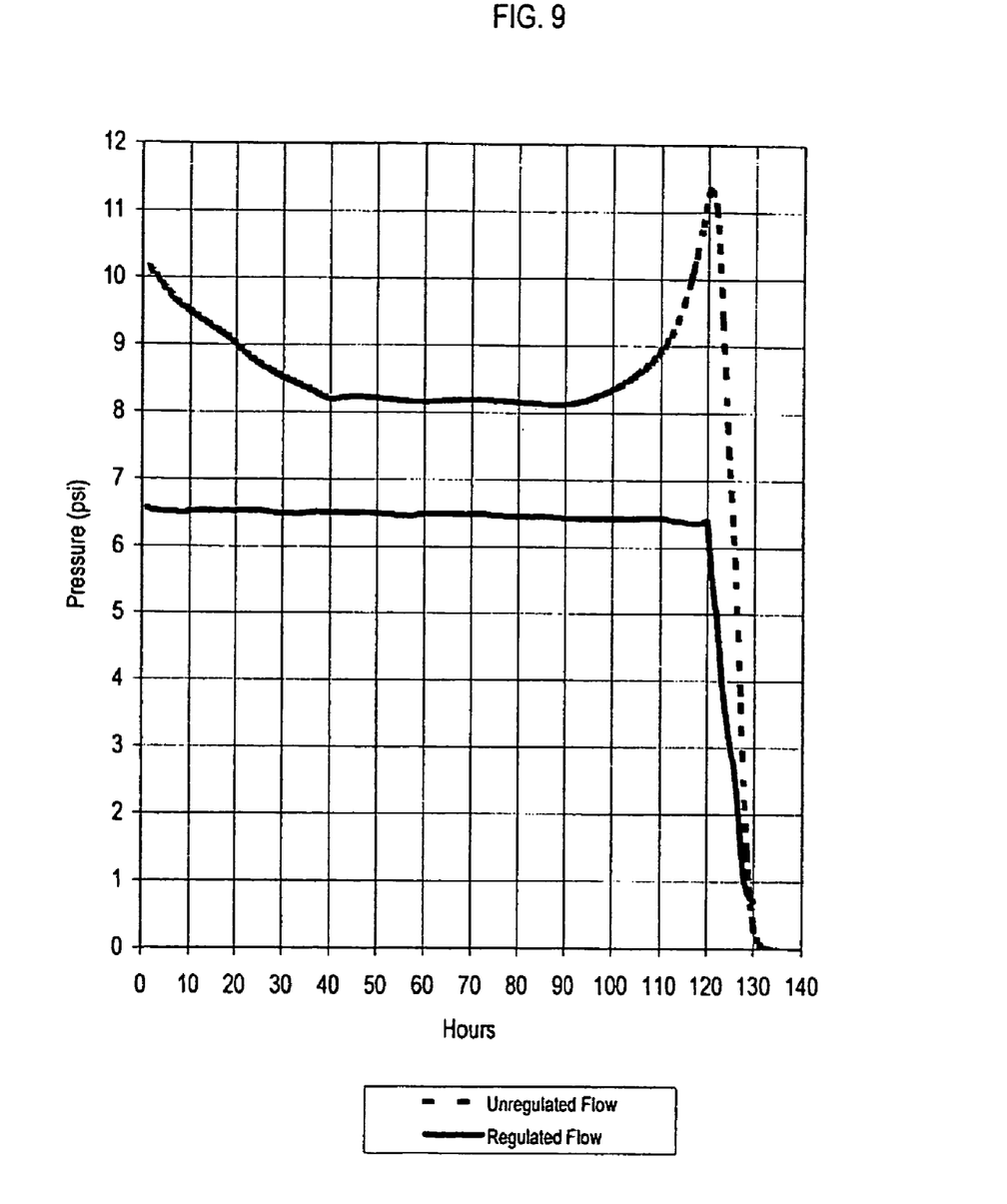
FIG. 9 is a graph showing a variance of fluid pressure at the regulator inlet caused by the bladder as the bladder empties in comparison to the outlet pressure of the regulator.

The invention has several advantages over the prior art. The flexible bladder enclosure 19 is more comfortable against the patient than a rigid housing. The closed or free end of the enclosure 19 is free to be folded over for more compact storage of the device. The pressure regulator 23 decreases the variability of the restrictor's operation in response to bladder pressure changes and thereby promotes a substantially constant fluid flow. In addition, the regulator may be adjusted during manufacture to achieve the desired or labelled flow rate. FIG. 9 is a graph of fluid pressure of fluid exiting the bladder 15 (y-axis) vs. time for unregulated flow from the bladder (upper dashed line) and for flow regulated by the pressure regulator 23 (lower solid line). The upper line of the graph shows that the bladder 15 causes significant fluid pressure variation over time, and the most significant variance is just prior to exhaustion of the fluid in the bladder. The pressure regulator 23 significantly reduces the pressure variation so that the fluid flow rate to the flow restrictor 25 and to the patient is substantially constant. Similarly, the flexible flow restrictor 25 is more comfortable against the patient than a rigid glass capillary. The flexible tubing 215 of the flow restrictor 25 is also advantageous because it is significantly less expensive than a conventional glass capillary.

In view of the above, it will be seen that the several objects of the invention are achieved and other advantageous results attained.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. An ambulatory infusion device for dispensing a fluid into a patient comprising:
   a bladder enclosure having a length and comprising a sheath of flexible material which is sufficiently flexible and collapsible along a substantial portion of the length, the sheath having a first open end defining a mouth and a second closed end, the first open end being affixed to a rigid closure;

a bladder support comprising a stem which extends into an elastic bladder secured in fixed position relative to said closure;

the elastic bladder mounted on the bladder support, the bladder being positioned inside the sheath and having an interior volume for storing the fluid under pressure;

the sheath extending from said closure toward the closed second end of the sheath spaced beyond said bladder, said closed second end of the sheath being free to conform to the body of the patient so that the device is comfortable when worn;

a pressure regulator in fluid communication with the bladder; and a flow restrictor in fluid communication with the pressure regulator and positioned downstream therefrom, the flow restrictor having an inlet for receiving the fluid at an inlet pressure and an outlet for discharging the fluid at an outlet pressure.

2. An infusion device as set forth in claim 1 wherein the flexible material of the sheath resiliently deforms when the bladder enlarges with fluid in response to increased pressure between the sheath and the bladder.

3. An infusion device as set forth in claim 1 wherein the flow restriction is formed of a flexible tubing having an inside diameter less than about 0.0003 inches.

4. An infusion device as set forth in claim 3 wherein the inside diameter of the tubing is sized about 0.0022 inches.

5. An infusion device as set forth in claim 4 further comprising intermediate tubing connecting the pressure regulator to the flow restrictor.

6. An infusion device as set forth in claim 5 wherein the flexible tubing is made of a polymer.

7. An infusion device as set forth in claim 6 wherein the length of the flexible tubing of the flow restrictor is determined based on the fluid pressure change from an inlet of the tubing to an outlet of the tubing.

8. A method of using the infusion device of claim 1 comprising securing the flow restrictor against the skin of a patient so as to promote a constant temperature of the flow restrictor.

9. A method of manufacturing the flow restrictor of claim 3 comprising measuring fluid flow resistance through a length of the flexible tubing and then trimming the length of the tubing based on the fluid flow resistance.

10. A method of manufacturing as set forth in claim 9 wherein the measuring step is performed by forcing pressurized air through the tubing and measuring the pressure difference from an inlet end to an outlet end of the tubing.

11. An infusion device as set forth in claim 1 wherein said closed second end of the sheath is free of attachment to said bladder support.

12. An infusion device as set forth in claim 1 wherein said closed second end of the sheath is freely movable so that the sheath is foldable on one or more fold lines extending generally transverse to the longitudinal axis of the sheath for more compact storage of the infusion device.

13. An infusion device as set forth in claim 12 wherein the sheath is formed of a resilient material, and wherein the bladder and the sheath stretch as the bladder is filled with fluid.

14. An infusion device as set forth in claim 12 wherein the sheath is adapted to collapse from an expanded condition when the bladder is full to an unexpanded condition as the fluid is being dispensed from the bladder.

15. An infusion device as set forth in claim 14 wherein the sheath has a folded shape in its unexpanded condition.

16. An infusion device as set forth in claim 15 wherein the sheath material is resilient so that the sheath tends to regain its folded shape as the sheath moves from the expanded condition to said unexpanded condition.

17. An infusion device as set forth in claim 16 wherein the sheath includes pleated opposing sides which fold inward toward the bladder as the sheath collapses to said unexpanded condition.

18. An infusion device as set forth in claim 1 wherein the sheath is adapted to collapse from an expanded condition when the bladder is full to an unexpanded condition as the fluid is being dispensed from the bladder.

19. An infusion device as set forth in claim 1 wherein the sheath is made of polyethylene.

20. An infusion device as set forth in claim 1 wherein the sheath is made of vinyl.

21. An infusion device as set forth in claim 1 wherein the rigid closure is generally rectangular and wherein the first end of the sheath is sealed around the closure.

22. An infusion device as set forth in claim 21 wherein the sheath has pleated opposing sides which fold inward toward the bladder as the sheath collapses from an expanded condition when the bladder is full to an unexpanded condition as the fluid is being dispensed from the bladder.

23. An infusion device as set forth in claim 22 wherein the sheath has a length which is greater than the length of the bladder in an unfilled condition to allow for lengthwise expansion of the bladder as it is filled.

24. An infusion device as set forth in claim 1 wherein said bladder support includes a stem extending into the sheath for mounting the bladder inside the sheath.

25. An infusion device as set forth in claim 24 wherein the bladder support further comprises a head on the stem mounted in an opening in said rigid closure, said device regulator disposed on the head of the bladder support.

* * * * *